United States Patent [19]

Shibata et al.

[11] Patent Number: 4,980,083
[45] Date of Patent: Dec. 25, 1990

[54] OPTICALLY ACTIVE COMPOUND AND LIQUID CRYSTAL COMPOSITION CONTAINING THE SAME

[75] Inventors: Toshihiro Shibata; Masaki Kimura, both of Urawa, Japan

[73] Assignee: Adeka Argus Chemical Co., Ltd., Tokyo, Japan

[21] Appl. No.: 480,168

[22] Filed: Feb. 14, 1990

[30] Foreign Application Priority Data

Feb. 14, 1989 [JP] Japan ................... 1-34749

[51] Int. Cl.$^5$ .................. G02F 1/13; C09K 19/34; C07D 239/02
[52] U.S. Cl. .................. 252/299.61; 252/299.01; 299/65, 66; 350/350 R, 350 S; 544/239, 335;
[58] Field of Search .................. 299/1, 6, 61, 62, 64, 299/65, 66; 350/350 R, 350 S; 544/339, 335; 560/39; 568/811, 902

[56] References Cited

U.S. PATENT DOCUMENTS

| | | | |
|---|---|---|---|
| 4,818,430 | 4/1989 | Saito et al. | 252/299.61 |
| 4,835,274 | 5/1989 | Kano | 544/239 |
| 4,882,083 | 11/1989 | Terashima et al. | 252/299.61 |
| 4,886,619 | 12/1989 | Janulis | 252/299.1 |
| 4,900,472 | 2/1990 | Miyazawa et al. | 252/299.61 |
| 4,900,473 | 2/1990 | Miyazawa et al. | 252/299.61 |
| 4,916,252 | 4/1990 | Sayo et al. | 560/39 |

FOREIGN PATENT DOCUMENTS 63-44548 2/1988 Japan .

*Primary Examiner*—John S. Maples
*Assistant Examiner*—Shean C. Wu
*Attorney, Agent, or Firm*—Young & Thompson

[57] ABSTRACT

An optically active compound useful as a component of a ferroelectric liquid crystal composition represented by the following general formula (I) and a ferroelectric liquid crystal composition containing the same:

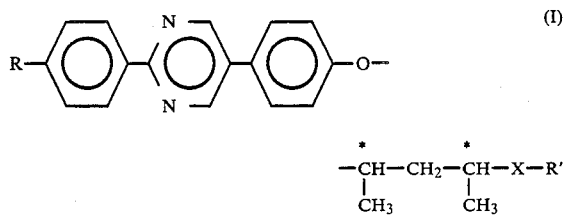

wherein R stands for a $C_{1\sim 18}$ alkyl group; R' stands for a $C_{1\sim 18}$ alkyl group which may be substituted or an aryl group; X stands for

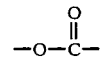

or —O— and an asterisk refers to an optically active carbon atom.

3 Claims, No Drawings

OPTICALLY ACTIVE COMPOUND AND LIQUID CRYSTAL COMPOSITION CONTAINING THE SAME

BACKGROUND OF THE INVENTION

1. Field of the Invention

The present invention relates to a novel optically active compound and a liquid crystal composition containing the same. More particularly, it relates to an optically active compound useful as a component of a ferroelectric liquid crystal composition and a ferroelectric liquid crystal composition containing the same.

2. Description of the Prior Art

Although the practical use of a liquid crystal element has started with the application thereof to the display of a watch or an electronic calculator, it is now applied to a wider field including pocketable televisions, various displays and optoelectronic elements. Most of the liquid crystal display elements now in use are of TN display type wherein nematic liquid crystal materials are used. Since this type of display is of photoreception type, it has disadvantages in that the speed of response is low and that the displayed images cannot be seen at some angles of vision, though it has advantages in that the eyes get little tired and that the power consumption is very low. In order to overcome these disadvantages, a display system using a ferroelectric liquid crystal has recently been proposed. Even in a display element of this type, like in the case of the above mentioned TN liquid crystal display element, a ferroelectric liquid crystal must be practically used in a state mixed with several liquid crystal or non-liquid-crystal compounds, i.e., as a so-called ferroelectric liquid crystal composition, in order to satisfy various characteristics.

On the basis of this idea, Japanese Patent Laid-Open No. 44548/1988 proposed the use of an optically active 2-methyl-1,3-propanediol compound as a component of a ferroelectric liquid crystal composition. However, such a ferroelectric liquid crystal composition is not sufficiently improved in the speed of response, if any. Accordingly, a further improvement in the speed of response of a ferroelectric liquid crystal composition has been expected in order to put the composition to practical use.

SUMMARY OF THE INVENTION

Under these circumstances, the inventors of the present invention have intensively studied to find out an optically active compound which can give a ferroelectric liquid crystal composition excellent in the speed of response and have found that a novel optically active compound represented by the following general formula (I) is very suitable for this object:

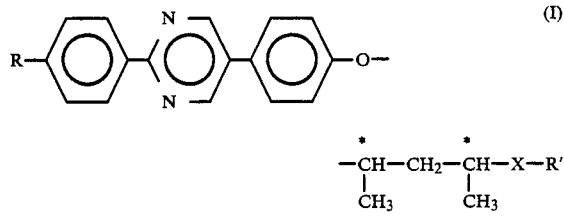

wherein R stands for a $C_{1\sim18}$ alkyl group; R' stands for a $C_{1\sim18}$ alkyl group which may be substituted or an aryl group; X stands for

or —O— and an asterisk refers to an optically active carbon atom.

The compound represented by the general formula (I) does not exhibit any liquid crystal phase near room temperature. However, when the compound is added to a matrix liquid crystal having an SmC or SmC* phase, it imparts a large spontaneous polarization to the SmC or SmC* phase while scarcely lowering the phase transition temperature of the matrix liquid crystal between SmA and SmC or SmC* to form a chiral smectic phase exhibiting a high-speed electric field response.

Accordingly, the compound of the present invention is useful as a component of a ferroelectric liquid crystal composition. Further, a ferroelectric liquid crystal composition containing the compound according to the present invention is also extremely useful in practical use.

DETAILED DESCRIPTION OF THE INVENTION

The compound represented by the general formula (I) will be described in more detail.

The $C_{1\sim18}$ alkyl group defined with respect to R includes methyl, ethyl, propyl, butyl, pentyl, hexyl, heptyl, octyl, nonyl, decyl, undecyl, lauryl, myristyl, palmityl and stearyl groups.

The $C_{1\sim18}$ alkyl group defined with respect to R', which may be substituted, includes those listed above with respect to R.

Although the optically active compound of the present invention represented by the general formula (I) does not always exhibit properties as a ferroelectric liquid crystal by itself, it may be mixed with other liquid crystal or non-liquid-crystal compounds to give a practically usable liquid crystal composition. Representative examples of the compound to be mixed include the following compounds, though not limited to them:

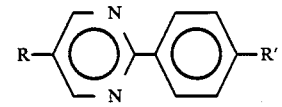

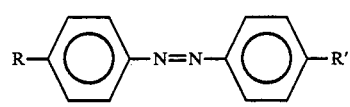

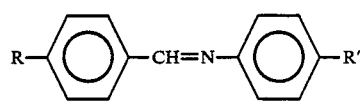

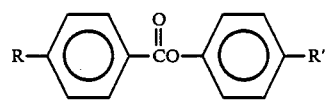

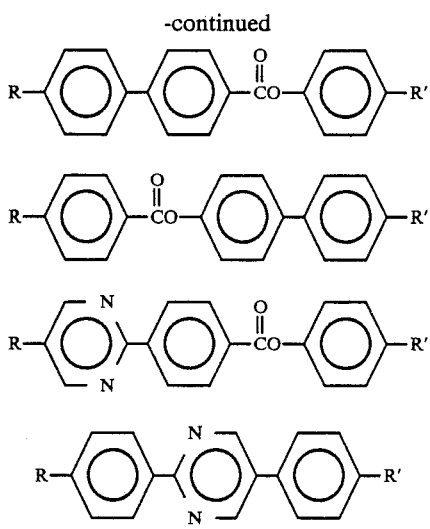

These compounds may also be used as a mixture of two or more of them in an arbitrary ratio depending upon the object of the use.

In the liquid crystal composition of the present invention, the optically active compound of the present invention is preferably used in an amount of 1 to 50 parts by weight, still preferably 5 to 40 parts by weight, per 100 parts by weight of a matrix liquid crystal (other liquid crystal or nonliquid-crystal compound).

The present invention will now be described by referring to the following Examples, though it is not limited by them.

EXAMPLE 1 (SYNTHESIS EXAMPLE 1)

Synthesis of (1″R,3″R)-2-(4′-n-octylphenyl)-5-[4′-(1″-methyl-3″-butanoyloxybutyloxy)phenyl]-pyrimidine (Compound No. 1)

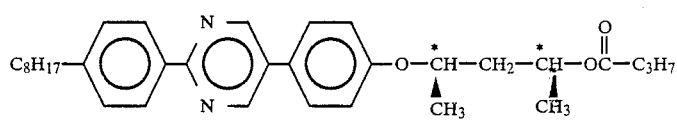

0.62 g of (S,S)-2,4-pentanediol, 1.80 g of 2-(4′-n-octylphenyl)-5-(4″-hydroxyphenyl)pyrimidine, 1.57 g of triphenylphosphine and 1.21 g of diisopropyl azodicarboxylate were dissolved in 25 ml of ethyl ether to obtain a solution. This solution was stirred at a room temperature for 2.5 hours. The triphenylphosphine oxide thus precipitated was filtered off and the filtrate was freed from the solvent. The solvent-free residue was purified by silica gel column chromatography using a n-hexane/ethyl acetate (7 : 3) mixture as a developing solvent to obtain 1.62 g of (1″R,3″S)-2-(4′-octylphenyl)-5-[4′-(1″-methyl-3″-hydroxybutyloxy)phenyl]pyrimidine.

Then, 0.90 g of the pyrimidine compound, 0.18 g of butyric acid, 1.31 g of triphenylphosphine and 1.01 g of diisopropyl azodicarboxylate were dissolved in 5 ml of ethyl ether. The obtained solution was stirred at a room temperature for 2 hours. The triphenylphosphine oxide thus formed was filtered off and the filtrate was freed from the solvent. The residue was purified by silica gel column chromatography using a n-hexane/ethyl acetate (80:20) mixture as a developing solvent to obtain 0.77 g of a colorless oil.

The infrared spectroscopic analysis of the oil revealed that the oil had the following characteristic absorptions and it was thus identified with the objective compound:

| 2950 cm$^{-1}$ (s), | 2890 cm$^{-1}$ (w), | 1735 cm$^{-1}$ (s), |
| --- | --- | --- |
| 1615 cm$^{-1}$ (m), | 1585 cm$^{-1}$ (m), | 1520 cm$^{-1}$ (m), |
| 1435 cm$^{-1}$ (s), | 1380 cm$^{-1}$ (m), | 1290 cm$^{-1}$ (m), |
| 1250 cm$^{-1}$ (s), | 1190 cm$^{-1}$ (m), | 1155 cm$^{-1}$ (w), |
| 1110 cm$^{-1}$ (w), | 840 cm$^{-1}$ (m), | 800 cm$^{-1}$ (w), |

EXAMPLE 2 (SYNTHESIS EXAMPLE 2)

Synthesis of (1″S,3″S)-2-(4′-n-octylphenyl)-5-[4′-(1″-methyl-3″-butanoyloxybutyloxy)phenyl]-pyrimidine (Compound No. 2)

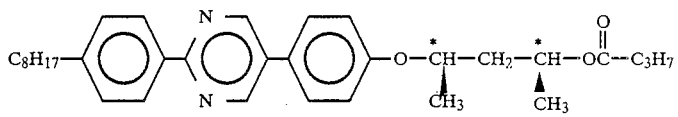

The same procedure as that of Example 1 was repeated except that (R,R)-2,4-pentanediol was used instead of the (S,S)-2,4-pentanediol to obtain a product.

The infrared spectroscopic analysis of the produce revealed that the product had the following characteristic absorptions and it was thus identified with the objective compound:

| 2950 cm$^{-1}$ (s), | 2890 cm$^{-1}$ (w), | 1735 cm$^{-1}$ (s), |
| --- | --- | --- |
| 1615 cm$^{-1}$ (m), | 1585 cm$^{-1}$ (m), | 1520 cm$^{-1}$ (m), |
| 1435 cm$^{-1}$ (s), | 1380 cm$^{-1}$ (m), | 1290 cm$^{-1}$ (m), |
| 1250 cm$^{-1}$ (s), | 1190 cm$^{-1}$ (m), | 1155 cm$^{-1}$ (w), |
| 1110 cm$^{-1}$ (w), | 840 cm$^{-1}$ (m), | 800 cm$^{-1}$ (w) |

EXAMPLE 3 (SYNTHESIS EXAMPLE 3)

Synthesis of (1″R,3″S)-2-(4′-n-octylphenyl)-5-[4′-(1″-methyl-3″-methoxybutyloxy)phenyl]pyrimidine (Compound No. 3)

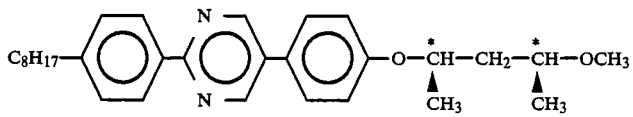

0.07 g of 55% sodium hydride was dispersed in 2 ml of dimethylformamide (DMF) to obtain a dispersion. A solution of 0.45 g of (1″R,3″R)-2-(4′-n-octylphenyl)-5-[4′-(1″-methyl-3″-hydroxybutyloxy)phenyl]pyrimidine in 2 ml of DMF was dropwise added to the dispersion. The obtained mixture was stirred at a room temperature for one hour, followed by the dropwise addition thereto of a solution of 0.23 g of methyl iodide in 2 ml of DMF. The obtained mixture was further stirred at a room temperature for 2 hours, followed by the addition of water. The mixture was extracted with ethyl ether and the extract was purified by silica gel column chromatography using a n-hexane/ethyl acetate (85:15) mixture as a developing solvent to obtain 0.37 g of a white solid.

The infrared spectroscopic analysis of the solid revealed that the solid had the following characteristic absorptions and it was thus identified with the objective compound.

| | | |
|---|---|---|
| 2920 cm$^{-1}$ (s), | 2850 cm$^{-1}$ (w), | 1610 cm$^{-1}$ (s), |
| 1580 cm$^{-1}$ (w), | 1530 cm$^{-1}$ (w), | 1510 cm$^{-1}$ (m), |
| 1430 cm$^{-1}$ (s), | 1375 cm$^{-1}$ (m), | 1280 cm$^{-1}$ (m), |
| 1245 cm$^{-1}$ (s), | 1180 cm$^{-1}$ (m), | 1090 cm$^{-1}$ (m), |
| 835 cm$^{-1}$ (m), | 795 cm$^{-1}$ (w) | |

The obtained compound was sandwitched between two glass plates and the phase of the compound was observed with a polarization microscope to ascertain the following phase transition:

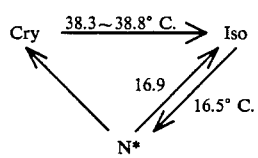

EXAMPLE 4 (SYNTHESIS EXAMPLE 4)

Synthesis of (1″S,3″R)-2-(4′-n-octylphenyl)-5-[4′-(1″-methyl-3″-methoxybutyloxy)phenyl]pyrimidine (Compound No. 4)

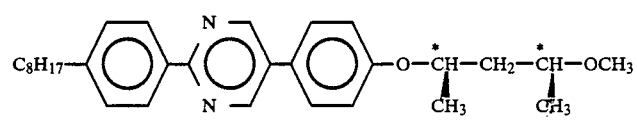

The same procedure as that of Example 3 was repeated except that (1″S,3″R)-2-(4′-n-octylphenyl)-5-[4′-(1″-methyl-3″-hydroxybutyloxy)phenyl]pyrimidine was used to obtain a product.

The infrared spectroscopic analysis of the product revealed that the product had the following characteristic absorptions and it was thus identified with the objective compound:

| | | |
|---|---|---|
| 2920 cm$^{-1}$ (s), | 2850 cm$^{-1}$ (w), | 1610 cm$^{-1}$ (s), |
| 1580 cm$^{-1}$ (w), | 1530 cm$^{-1}$ (w), | 1510 cm$^{-1}$ (m), |
| 1430 cm$^{-1}$ (s), | 1375 cm$^{-1}$ (m), | 1280 cm$^{-1}$ (m), |
| 1245 cm$^{-1}$ (s), | 1180 cm$^{-1}$ (m), | 1090 cm$^{-1}$ (m), |
| 835 cm$^{-1}$ (m), | 795 cm$^{-1}$ (w) | |

EXAMPLE 5 (SYNTHESIS EXAMPLE 5)

Synthesis of (1″R,3″S)-2-(4′-n-octylphenyl)-(1″-methyl-3″-hexyloxybutyloxy)phenyl]pyrimidine (Compound No. 5)

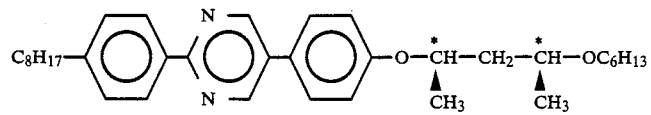

0.07 g of 55% sodium hydride was dispersed in 2ml of dimethylformamide (DMF) to obtain a dispersion. A solution of 0.45 g of (1″R,3″S)-2-(4′-n-octylphenyl)-(1″-methyl-3″-hydroxybutyloxy)phenyl]pyrimidine in 2 ml of DMF was dropwise added to the dispersion. The obtained mixture was stirred at a room temperature for one hour, followed by the dropwise addition thereto of a solution of 0.26 g of n-hexyl bromide in 2 ml of DMF. The obtained mixture was further stirred at 90° C. for 2 hours, followed by the addition of water. The obtained mixture was extracted with ethyl ether and the extract was dried and freed from the solvent. The residue was purified by silica gel column chromatography using a n-hexane/ethyl acetate (90:10) mixture as a developing solvent to obtain 0.14 g of a colorless viscous liquid.

The infrared spectroscopic analysis of the liquid revealed that the liquid had the following characteristic absorptions and it was thus identified with the objective compound:

| | | |
|---|---|---|
| 2925 cm$^{-1}$ (s), | 2860 cm$^{-1}$ (m), | 1650 cm$^{-1}$ (m), |
| 1585 cm$^{-1}$ (w), | 1515 cm$^{-1}$ (w), | 1430 cm$^{-1}$ (s), |
| 1375 cm$^{-1}$ (w), | 1285 cm$^{-1}$ (w), | 1250 cm$^{-1}$ (s), |
| 1185 cm$^{-1}$ (w), | 1130 cm$^{-1}$ (w), | 1110 cm$^{-1}$ (w), |
| 835 cm$^{-1}$ (w), | 795 cm$^{-1}$ (w) | |

EXAMPLE 6 (SYNTHESIS EXAMPLE 6)

Synthesis of (1″R,3″R)-2-(4′-n-octylphenyl)-5-[4′-(1″-methyl-3″-phenoxybutyloxy)phenyl]pyrimidine (Compound No. 6)

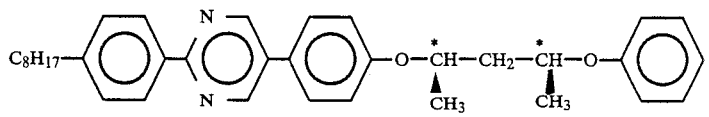

0.45 g of (1″R,3″S)-2-(4′-n-octylphenyl)-5[4′-(1″-methyl-3″-hydroxybutyloxy)phenyl]pyrimidine, 0.11 g of phenol, 0.31 g of triphenylphosphine and 0.24 g of diisopropyl azodicarboxylate were dissolved in 5 ml of ethyl ether. The obtained solution was stirred at a room temperature for 3 hours. The triphenylphosphine oxide thus precipitated was filtered off and the filtrate was freed from the solvent. The residue was purified by silica gel column chromatography using a n-hexane/ethyl acetate (90:10) mixture as a developing solvent to obtain 0.20 g of a colorless liquid.

The infrared spectroscopic analysis of the liquid revealed that the liquid had the following characteristic absorptions and it was thus identified with the objective compound:

| 2920 cm$^{-1}$ (s), | 2850 cm$^{-1}$ (w), | 1610 cm$^{-1}$ (s), |
|---|---|---|
| 1585 cm$^{-1}$ (m), | 1515 cm$^{-1}$ (m), | 1495 cm$^{-1}$ (m), |
| 1430 cm$^{-1}$ (s), | 1375 cm$^{-1}$ (m), | 1280 cm$^{-1}$ (m), |
| 1240 cm$^{-1}$ (s), | 1180 cm$^{-1}$ (m), | 1110 cm$^{-1}$ (m), |
| 830 cm$^{-1}$ (m), | 790 cm$^{-1}$ (w), | 755 cm$^{-1}$ (m), |
| 695 cm$^{-1}$ (w) | | |

EXAMPLE 7 (APPLICATION EXAMPLE 1)

In order to evaluate the effect the liquid crystal composition according to the present invention, the following four compounds were mixed with each other to obtain a matrix liquid crystal composition:

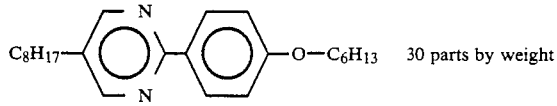 30 parts by weight

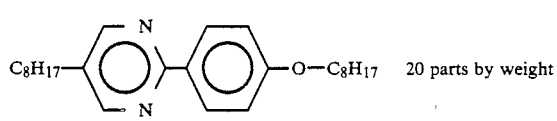 20 parts by weight

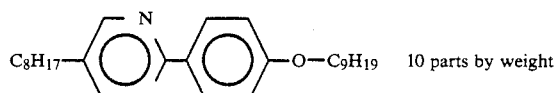 10 parts by weight

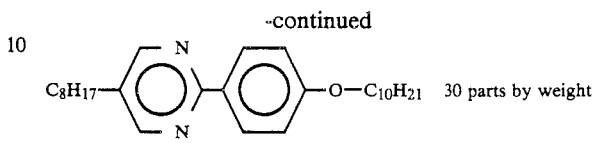 30 parts by weight

The above matrix liquid crystal composition was sandwitched between two glass plates and the phase of the composition was observed with a polarization microscope to ascertain the following phase transition:

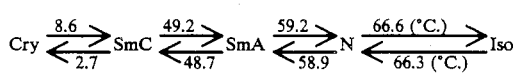

90% by weight of the matrix liquid crystal composition was mixed with 10% by weight of each of the compounds of the present invention prepared in Examples 1 to 6 to obtain liquid crystal compositions. The phase transition temperatures of the liquid crystal compositions were determined by the use of a polarization microscope in a similar manner to that described above with respect to the matrix liquid crystal composition. Further, the liquid crystal compositions were each injected into a glass cell of 2-μm thickness which was fitted with a transparent electrode and the surface of which was coated with a polyimide orientation film subjected to the parallel orientation treatment by rubbing to obtain a liquid crystal display element. The liquid crystal display elements thus prepared were examined for the speed of response (Ps) at 30° C. by applying an electric field of ±15 V (60 Hz rectangular alternating current) thereto. Further, the spontaneous polarizations thereof were determined by the triangular wave method. The results are shown in Table 1.

TABLE 1

| | | | | | | | 30° C. | |
|---|---|---|---|---|---|---|---|---|
| No. | SmC* | | SmA | | N* | | Iso | τ (μsec) | Ps (nC/cm$^2$) |
| Compound No. 1 | • | 45.6 | • | 53.5 | • | 63.0 | • | 110 | +8.9 |
| Compound No. 2 | • | 45.6 | • | 53.5 | • | 63.0 | • | 110 | −8.9 |
| Compound No. 3 | • | 48.4 | • | 55.8 | • | 64.5 | • | 125 | +6.1 |
| Compound No. 4 | • | 48.4 | • | 55.8 | • | 64.5 | • | 125 | −6.1 |
| Compound No. 5 | • | 47.7 | • | 56.5 | • | 63.4 | • | 172 | +0.87 |
| Compound No. 6 | • | 41.3 | • | 51.7 | • | 62.2 | • | 308 | +0.36 |

Conditions: The phase transition temperatures were each determined by polarization microscopy.

polyimide orientation film, cell thickness: 2 μm, application of ±15 V (60 Hz), Ps was determined by the triangular wave method.

It can be understood from the results shown in Table 1 that the optically active compound of the present invention induces an SmC* phase to bring about an extremely short response time and a large spontaneous polarization even when it is added to a matrix liquid crystal composition only in an amount of 10%.

EXAMPLE 8 (APPLICATION EXAMPLE 2)

Compositions obtained by adding 10 to 30% of a compound of the present invention represented by the formula which will be described below to the same matrix liquid crystal composition as that used in Example 7 were each examined for phase transition temperature, speed of response and change in spontaneous polarization. The results are shown in Table 2.

TABLE 2

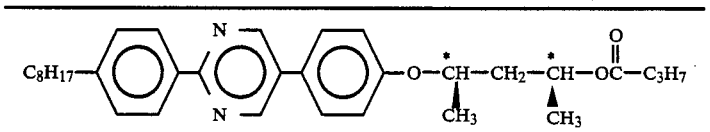

| Amount | SmC* | | SmA | | N* | | Iso | 30° C. τ (μsec) | Ps (nC/cm$^2$) |
|---|---|---|---|---|---|---|---|---|---|
| 10% | . | 46 | . | 54 | . | 63 | . | 110 | −8.9 |
| 20% | . | 43 | . | 47 | . | 60 | . | 80 | −10.9 |
| 30% | . | 36 | . | — | . | 56 | . | 80 | −26.3 |

Conditions: The phase transition temperatures were each determined by polarization microscopy.
polyimide orientation film, cell thickness: 2 μm, application of ±15 V (60 Hz), Ps was determined by the triangular wave method.

Example 9 (APPLICATION EXAMPLE 3)

The same matrix liquid crystal composition (A) as that used in Example 7 was mixed with a chlorinated pyrimidine compound (B) represented by the formula which will be described below and the Compound No. 1 (C) prepared in Example 1 at a ratio as specified below to obtain a liquid crystal composition. The liquid crystal compositions thus prepared were each examined for phase transition temperatures, speed of response and change in spontaneous polarization. The results are shown in Table 3.

[Chlorinated pyrimidine compound]

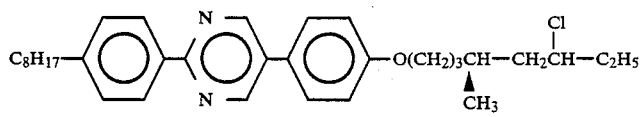

[Formulation]

| Compound | A | B | C |
|---|---|---|---|
| Ex. 9-1 | 60 parts | 20 parts | 20 parts |
| 9-2 | 70 | 15 | 15 |
| 9-3 | 70 | 20 | 10 |
| 9-4 | 79 | 14 | 7 |
| Ref. Ex. 9-1 | 80 | 20 | — |
| 9-2 | 90 | 10 | — |

TABLE 3

| No. | SmC* | | SmA | | N* | | Iso | 30° C. τ (μsec) | Ps (nC/cm$^2$) |
|---|---|---|---|---|---|---|---|---|---|
| Ex. | | | | | | | | | |
| 9-1 | • | 55 | • | 66 | • | 70 | • | 79 | +24.5 |
| 9-2 | • | 53 | • | 64 | • | 69 | • | 83 | +11.5 |
| 9-3 | • | 58 | • | — | • | 75 | • | 90 | +21.8 |
| 9-4 | • | 53 | • | 67 | • | 70 | • | 78 | +8.0 |
| Ref. Ex. | | | | | | | | | |
| 9-1 | • | 58 | • | 75 | • | — | • | 108 | +5.2 |

TABLE 3-continued

| No. | SmC* | | SmA | | N* | | Iso | 30° C. τ (μsec) | Ps (nC/cm$^2$) |
|---|---|---|---|---|---|---|---|---|---|
| 9-2 | • | 52 | • | 68 | • | 71 | • | 165 | +1.5 |

Conditions: The phase transition temperatures were each determined by polarization microscopy.
polyimide orientation film, cell thickness: 2 μm, application of ±15 V (60 Hz), Ps was determined by the triangular wave method.

EXAMPLE 10 (APPLICATION EXAMPLE 4)

A liquid crystal composition comprising 70 parts of the same matrix liquid crystal composition as that used in Example 7, 15 parts of the same chlorinated pyrimidine compound as that used in Example 9 and 15 parts of the Compound No. 3 prepared in Example 3 exhibited the following phase transition temperatures:

The above liquid crystal composition was injected into a glass cell of 2-μm thickness which is fitted with a transparent electrode and the surface of which was coated with a polyimide orientation film subjected to the parallel orientation treatment by rubbing to obtain a liquid crystal display element. This liquid crystal display element was examined for speed of response (Ps) at 30° C. by applying an electric field of ±15 V (60 Hz rectangular alternating current) thereto. Further, the spontaneous polarization (τ) thereof was determined by the triangular wave method. The speed of response (Ps)

was -11.1 nC/cm² and the spontaneous polarization (τ) was 106 μsec.

As shown in the foregoing Examples 7 to 10, when the compound of the present invention is added to a matrix liquid crystal having an SmC or SmC* phase, the compound imparts a large spontaneous polarization to the SmC or SmC* phase while scarcely lowering the transition temperature of the matrix crystal between SmA and SmC or SmC*, thus forming a chiral smectic C phase exhibiting a high-speed electric field response, though the compound does not exhibit any liquid crystal phase near room temperature.

What is claimed is:

1. An optically active compound represented by the following general formula (I):

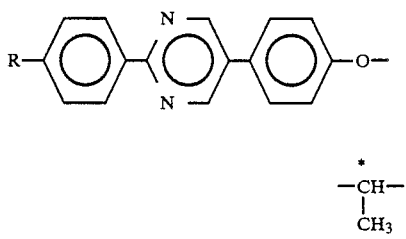

wherein R stands for a $C_{1\sim18}$ alkyl group; R' stands for a $C_{\sim18}$ alkyl group which may be substituted or an aryl group; X stands for

—O— and an asterisk refers to an optically active carbon atom.

2. A ferroelectric liquid crystal composition containing at least one optically active compound represented by the following general formula (I):

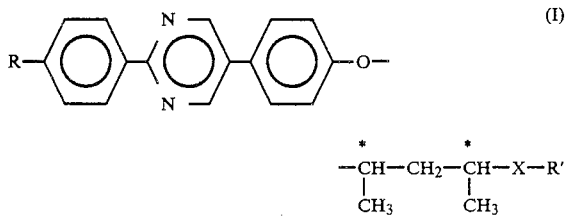

wherein R stands for a $C_{1\sim18}$ alkyl group; R' stands for a $C_{1\sim18}$ alkyl group which may be substituted or an aryl group; X stands for $$-O-\overset{\overset{O}{\|}}{C}-$$

or —O— and an asterisk refers to an optically active carbon atom, as a component.

3. A ferroelectric liquid crystal composition as set forth in claim 2 wherein the optically active compound represented by the general formula (I) is contained in an amount of 1 to 50 parts by weight per 100 parts by weight of a matrix liquid crystal wherein matrix liquid crystal is a liquid crystal or non-liquid-crystal compound other than the optically active compound.

* * * * *